(12) United States Patent
Prien et al.

(10) Patent No.: US 11,592,436 B2
(45) Date of Patent: Feb. 28, 2023

(54) SYSTEM AND METHOD FOR NON-INVASIVE EMBRYO SEXING

(71) Applicant: TEXAS TECH UNIVERSITY SYSTEM, Lubbock, TX (US)

(72) Inventors: Samuel D. Prien, Shallowater, TX (US); Lindsay L. Penrose, Lubbock, TX (US); Cara E. Wessels, Dripping Springs, TX (US)

(73) Assignee: Texas Tech University System, Lubbock, TX (US)

( * ) Notice: Subject to any disclaimer, the term of this patent is extended or adjusted under 35 U.S.C. 154(b) by 374 days.

(21) Appl. No.: 17/044,198

(22) PCT Filed: Mar. 29, 2019

(86) PCT No.: PCT/US2019/024995
§ 371 (c)(1),
(2) Date: Sep. 30, 2020

(87) PCT Pub. No.: WO2019/191682
PCT Pub. Date: Oct. 3, 2019

(65) Prior Publication Data
US 2021/0116435 A1 Apr. 22, 2021

Related U.S. Application Data

(60) Provisional application No. 62/650,638, filed on Mar. 30, 2018.

(51) Int. Cl.
*G01N 33/483* (2006.01)

(52) U.S. Cl.
CPC ................ *G01N 33/4833* (2013.01)

(58) Field of Classification Search
CPC ............ G01N 33/4833; G01N 33/483
See application file for complete search history.

(56) References Cited

FOREIGN PATENT DOCUMENTS

WO  2016004107 A1   1/2016
WO  WO-2016004107 A1 *  1/2016  ........... C12N 5/0604

OTHER PUBLICATIONS

American Association of Bioanalysts, Participant Statistics "Embryo Grading", Proficiency Testing Services, First Shipment 2013; 2 pages.

(Continued)

*Primary Examiner* — Jennifer Wecker
*Assistant Examiner* — Oyeleye Alexander Alabi
(74) *Attorney, Agent, or Firm* — Dickinson Wright PLLC; Kristopher Lance Anderson

(57) ABSTRACT

Disclosed is a system and device for determining sex of an embryo utilizing a non-invasive grading of early stage embryos (pre-hatching) based upon specific gravity, density and/or estimated weight. The device comprises a drop chamber having a lumen, capable of assessing characteristics of at least one embryo while descending. The system allows 100% recovery of embryos. A processor is further capable of performing assessment of the embryos. The disclosed system supports a wide variety of scenarios for human and animal reproductive technologies and related products and services.

17 Claims, 6 Drawing Sheets

(56) References Cited

OTHER PUBLICATIONS

Abe et al. "Accumulation of Cytoplasmic Lipid Droplets in Bovine Embryos and Cryotolerance of Embryos Developed in Different Culture Systems Using Serum-Free or Serum-Containing Media" Molecular Reproduction and Development, 61: 57-66, 2002, 10 pages.
Al-Inany et al. "Meta-analysis of recombinant versus urinary-derived FSH:an update" European Society of Human Reproduction and Embryology, vol. 18, No. 2 pp. 305-313, 2003, 9 pages.
Alfarawati et al. "First births after preimplantation genetic diagnosis of structural chromosome abnormalities using comparative genomic hybridization and microarray analysis" Human Reproduction, vol. 26, No. 6 pp. 1560-1574, 2011, 15 pages.
Alfarawati et al. "The relationship between blastocyst morphology, chromosomal abnormality, and embryo gender" Fertility and Sterility vol. 95, No. 2, Feb. 2011, 5 pages.
Baltz, Jay M. "Connections between preimplantation embryo physiology and culture" J Assist Reprod Genet (2013 30:1001-1007, 7 pages.
Barcelo-Fimbres et al. "Effects of Either Glucose or Fructose and Metabolic Regulators on Bovine Embryo Development and Lipid Accumulation In Vitro" Molecular Reproduction and Development 74:1406-1418, 2007, 13 pages.
Brezina, Paul R. "Preimplantation Genetic Testing in the 21st Century:Uncharted Territory" Clinical Medicine Insights: Reproductive Health, 2013, vol. 7 17-21, 5 pages.
Brison et al. "Identification of viable embryos in IVF by non-invasive measurement of amino acid turnover" Human Reproduction vol. 19, No. 10 pp. 2319-2324, 2004, 6 pages.
Buhler et al. "Recombinant human LH supplementation versus supplementation with urinary hCG-based LH activity during controlled ovarian stimulation in the long GnRH-agonist protocol: a matched case-control study" Gynecological Endocrinology, 2012, 28(5): 345-350, 7 pages.
Centers for Disease Control—Assisted Reproductive Technologies (ART). 2013. http://www.cdc.gov/art/.
Chandra et al. "Fertility, Family Planning, and Reproductive Health of U.S. Women: Data From the 2002 National Survey of Family Growth" U.S. Department of Health and Human Services, Vital and Health Statistics, Series 23, No. 25, Dec. 2005, 174 pages.
Chavez et al. "Dynamic blastomere behaviour reflects human embryo ploidy by the four-cell stage" Nature Communications, 2012;3:1251. doi: 10.1038/ncomms2249, 13 pages.
Conaghan et al. "Improving embryo selection using a computer-automated time-lapse image analysis test plus day 3 morphology: results from a prospective multicenter trial" Fertility and Sterility, 2013;100:412-9.e5. doi: 10.1016/j.fertnstert.2013.04.021, 13 pages.
Das et al. "Recurrent implantation failure: gamete and embryo factors" Fertility and Sterility, May 2012;97(5):1021-7. doi: 10 1016/j.fertnstert.2012.02.029, 7 pages.
Deonandan etal. "Toward a more meaningful in vitro fertilization success rate" Journal of Assist Reproduction and Genetics Oct. 2000;17(9):498-503, 6 pages.
Ercan et al. "Pregnancy outcomes in a university hospital after legal requirement for single-embryo transfer" Europena Journal of Obstetrics & Gynecology and Reproductive Biology 2014; pii: S0301-2115(14)00031-1. doi: 10.1016/j.ejogrb.2014.01.008, 4 pages.
Filicori et al. "Comparison of controlled ovarian stimulation with human menopausal gonadotropin or recombinant follicle-stimulating hormone" Fertility and Sterility, 2003;80:390-397. doi: 10.1016/S0015-0282(03)00594-6, 8 pages.
Gardner "Assessment of embryo viability prior to transfer by the noninvasive measurement of glucose uptake" Journal of Experimental Zoology 1987; 242:103-105, 4 pages.
Gardner et al. "Analysis of metabolism to select viable human embryos for transfer" Fertility and Sterility, Mar. 15, 2013;99(4):1062-72. doi: 10.1016/j.fertnstert.2012.12.004, 11 pages.
Gerer et al. "Effects of transfer of embryos independently cultured in essential and sequential culture media on pregnancy rates in assisted reproduction cycles" Journal of Assist Reproduction and Genetics, 2012 29:1097-1101, 5 pages.
Gerris et al. "Prevention of twin pregnancy after in-vitro fertilization or intracytoplasmic sperm injection based on strict embryo criteria: a prospective randomized clinical trial" Human Reproduction 1999; 14:2581-2587, 7 pages.
Grace et al. "Three hundred and thirty cycles of preimplantation genetic diagnosis for serious genetic disease: clinical considerations affecting outcome" BJOG. 2006;113:1393-401, 9 pages.
Houghton et al. "Non-invasive amino acid turnover predicts human embryo developmental capacity" Human Reprodruction 2002; 17:999-1005, 2 pages.
Hur et al. "Effect of micro-vibration culture system on embryo development" Journal of Assist Reproduction and Genetics 2013;30:835-41. doi: 10.1007/S10815-013-0007-0, 7 pages.
Kresowik et al. "Clinical factors associated with live birth after single embryo transfer" Fertility and Sterility, 2012;98:1152-6. doi: 10.1016/j.fertnstert.2012.07.1141, 5 pages.
Janvier et al. "The Epidemic of Multiple Gestations and Neonatal Intensive Care Unit Use: The Cost of Irresponsibility" The Journal of Pediatrics 2011; 159:409-13, 5 pages.
Jones, Gayle "Glucose metabolism of human morula and blastocyst-stage embryos and its relationship to viability after transfer" Reproductive BioMedicine Online 2001; 3:124-132, 9 pages.
Lane et al. "Selection of viable mouse blastocysts prior to transfer using a metabolic criterion" Human Reproduction 1996; 11:1975-1978, 4 pages.
Luke et al. "Cumulative birth rates with linked assisted reproductive technology cycles" The New England Journal of Medicine 2012;366:2483-91. doi: 10.1056/NEJMoa1110238, 10 pages.
Machtinger et al. "Morphological systems of human embryo assessment and clinical evidence" Reproductive BioMedicine Online. 2013;3:210-21. doi: 10.1016/j.rbmo.2012.10.021, 12 pages.
McArthur et al. "Pregnancies and live births after trophectoderm biopsy and preimplantation genetic testing of human blastocysts" Fertility and Sterility 2005;84:1628-36, 9 pages.
Munoz et al. "Influence of dietary protein restriction on ovulation, fertilization rates and pre-implantation embryonic development in mice" Journal of Experimental Zoology 1979 ;210:253-257, 6 pages.
Racowsky et al. "Standardization of grading embryo morphology" Journal of Assist Reproduction and Genetics 2010 ;27:437-9. doi: 10.1007/s10815-010-9443-2, 3 pages.
Reynolds et al. "Cycle cancellation and pregnancy after luteal estradiol priming in women defined as poor responders: a systematic review and meta-analysis" Human Reproduction 2013;28:2981-9. doi: 10.1093/humrep/det306, 9 pages.
Sakkas et al. "Noninvasive methods to assess embryo quality" Current Opinion in Obstetrics and Gynecology 2005;17:283-288, 6 pages.
Scott et al. "Blastocyst biopsy with comprehensive chromosome screening and fresh embryo transfer significantly increases in vitro fertilization implantation and delivery rates: a randomized controlled trial" Fertility and Sterility, 2013;100:697-703. doi: 10.1016/j.fertnstert.2013.04.035, 7 pages.
Staessen et al. "Comparison of blastocyst transfer with and without preimplantation genetic diagnosis for aneuploidy screening in couples with advanced maternal age: a prospective randomized controlled trial" Human Reproduction 2004, 19:2849-2858, 10 pages.
Steptoe et al. "Clinical aspects of pregnancies established with cleaving embryos grown in vitro" British Journal of Obstetrics and Gynaecology 1980;87:757-68, 12 pages.
Smith, A.L. "Blastocyst culture in human IVF: the final destination or a stop along the way?" Theriogenology. 2002;57:97-107, 11 pages.
Smith et al. "Advances in embryo culture systems" Seminars in Reproductive Medicine 2012;30:214-21. doi: 10.1055/s-0032-1311523., 8 pages.
Thompson et al. "Blastocyst expansion score and trophectoderm morphology strongly predict successful clinical pregnancy and live birth following elective single embryo blastocyst transfer (eSET): a

(56) References Cited

OTHER PUBLICATIONS national study" Journal of Assist Reproduction and Genetics 2013;12:1577-81. doi: 10.1007/s10815-013-0100-4, 5 pages.
Van Den Abbeel et al. "Association between blastocyst morphology and outcome of single-blastocyst transfer" Reproductive BioMedicine Online. 2013; 4:353-61. doi: 10.1016/j.rbmo.2013.07.006, 9 pages.
Weathers, Julie "Early Indications of Breed Differences for Cryopreservation of Embryos in Cattle" Master's Thesis in Animal Science, 2008, 56 pages.
Weathers et al. "The relationship between maternal body fat and pre-implantation embryonic weight: Implications for survival and long-term development in an assisted reproductive environment" Open Journal of Obstetrics and Gynecology 2013, 3; 1-5. doi:10.4236/ojog.2013.35A2001, 5 pages.
International Searching Authority, Search Report and the Written Opinion for PCT/US2019/024995, dated Aug. 8, 2019, 17 pages.
Bronet et al. "Is there a relationship between time-lapse parameters and embryo sex?" Fertility and Sterility 2015, vol. 103 No. 2, 8 pages.
Prien et al. "Preliminary trials of a specific gravity technique in the determination of early embryo growth potential" Human Reproduction, vol. 30, No. 9, pp. 2076-2083, 2015, 8 pages.
Wessels, C.E. "Noninvasive Embryo Assessment Technique to Predict Embryo Cryodamage and Potential Sex Selection" Journal of Animal Science, vol. 95, 2016, pp. 22-23, 2 pages.

\* cited by examiner

SYSTEM AND METHOD FOR NON-INVASIVE EMBRYO SEXING

CROSS-REFERENCE TO RELATED APPLICATIONS

This application is a 35 U.S.C § 371 national application of PCT Application Serial No. PCT/US2019/024995, filed on Mar. 29, 2019, entitled "System And Method For Non-Invasive Embryo Sexing", which claims priority to U.S. Provisional Patent Application Ser. No. 62/650,638, filed on Mar. 30, 2018, entitled "System And Method For Non-Invasive Embryo Sexing" and which patent applications are commonly owned by the owner of the present invention. These patent applications are hereby incorporated herein by reference in their entirety for all purposes.

TECHNICAL FIELD

The present invention relates in general to the field of assisted reproductive technologies (ART). In particular, the system provides for sexing of embryos. The disclosed systems and methods support a wide variety of scenarios for human reproductive medicine and animal husbandry related products and services.

STATEMENT OF FEDERALLY FUNDED RESEARCH

None.

BACKGROUND

Assisted reproductive technologies (ARTs) were developed originally to treat individuals with obstructed tubes, but have matured to procedures which, according to the U.S. Center for Disease Control (2013), now accounts for up to 2% of the annual U.S. birth rate. Since the first human birth from in vitro fertilization (IVF) in 1978, there have been significant improvements in stimulation protocols, fertilization and culture techniques, use of donor gametes and embryos, and patient selection. Further, the use of pre-implantation genetic testing (PGT), an invasive harvesting of cells for genetic screening, has allowed improved selection of embryos to avoid aneuploidy and other genetic defects. These improvements resulted in constantly increasing pregnancy rates while allowing a steady decrease in the number of embryos transferred (Center for Disease Control, 2013).

However, even with the dramatic improvement in pregnancy rates from ART over the last 35 years, two issues remain problematic for patients and healthcare professionals using ART: 1) multiple gestations and 2) the fecundity of individual embryos. To solve the first of these issues, ART has embraced the routine use of single embryo transfer (SET). The introduction of techniques for identifying embryos that have a higher chance of surviving based on their specific gravity, as taught by the Patent Cooperation Treaty (PCT) Application PCT/US2015/038665, incorporated by reference in its entirety, has allowed for SET to occur with increased efficiency and success, as embryos that meet the specific gravity criteria based on flowing through the apparatus below can be selected for single embryo transfer and reduce unwanted multiple gestations.

Continued development of ART and other reproductive technologies has focused further on yet another objective: sexing of embryos, and there are currently several approaches in the art. However, despite such advances, there remains a need to further enhance embryo selection by efficient and cost effective sex selection. Current approaches are expensive and time-consuming, are often invasive, and often require genetic screening, high levels of expertise in identification, or samples that must be sent to reference laboratories. Ideally, rapid, onsite and non-invasive approaches with the use of known devices, can maximize implementation in a cost-effective manner.

SUMMARY

It is therefore an object of the present invention to determine observed differences in estimated weight within a cohort of embryos to select the gender, also known as 'sexing', embryos for ART procedures and related applications. The present invention determines differences seen in estimated blastocyst weights, particularly via specific gravity measurements to determine sex of the embryos.

The present invention addresses the limitations of the art by providing a system for the non-invasive sexing of early stage embryos (pre-hatching) based upon specific gravity, density and/or estimated weight. The system allows 100% recovery of embryos and can detect sex at the earliest stages of development. The system may include drop chamber extending into to a collection pool to allow for recovery of embryos. Further, the system can be filled with an embryo culture media or cryoprotective media of users choosing and compatible with embryo survival outside of controlled culture conditions.

It is therefore an object of the present invention to provide a device and related system and method for sexing mammalian embryos, comprising: a base having an internal collection pool; a drop chamber extending vertically from the base; and a biocompatible media composition; wherein the drop chamber comprises a lumen for passing embryos for purposes of said assessment.

It is another object of the present invention to provide a method of sexing mammalian embryos, comprising: passing at least one embryo through a chamber comprising a lumen extending vertically from a media collection pool; and sexing the embryos by observing said descent through said chamber.

The system of the present invention may further include a pressure seal to allow the media to be continuous from the top of the drop chamber to collection pool. The system has a "timing zone" to determine the descent time of the embryo over a known distance.

Additionally, the system drains media from the drop chamber into the recovery pool, which may be referred to as a collection pool, upon breaking of the pressure seal to ensure flushing of the embryo into the recovery pool. Alternatively, the drop chamber itself may serve as a storage receptacle for later recovery of embryos. The system may further comprise rotating, revolving, carousel, or otherwise multiple-welled or multiple-strawed configurations, allowing for the ability of the drop chamber to have multiple chambers, each having its own collection pool, or collection pool to allow collection of information about individual embryos, such as sexing. In another aspect, the system provides the ability to have a single drop chamber positioned at various times over multiple collection pools to allow collection of information about individual embryos while allowing a single chamber's use.

It is therefore an object of the present invention provides a device for non-invasive determination of sex of a mammalian embryo, comprising: a drop chamber comprising a lumen extending vertically from the base capable of descending at least one embryo through the lumen; a base having an internal recovery pool capable of recovery of the at least one embryo; and a biocompatible media composition; wherein the drop chamber comprises a lumen for passing at least one embryo for measurement of specific gravity of the at least one embryo by descent time of the at least one embryo through the biocompatible media, wherein the specific gravity measurement is operable for determination of the applicable sex of the at least one embryo. In one aspect the measurement is a quantitative assessment of the at least one embryo density or buoyancy using specific gravity. In another aspect, the measurement is manual observation or automated.

The present invention may further comprise an automated measurement device comprising: a processor; a sensor coupled to the processor, wherein the optical system is capable of observation of the descent of the at least one embryo through the drop chamber comprising the lumen; and a memory coupled to the processor, the memory storing computer-readable instructions that are executable by the processor to cause a computer to execute operations comprising: capturing, by way of the sensor, data relating to the descent time of the at least one embryo obtained from measuring the descending at least one embryo; processing the data relating to the descent time of the at least one embryo to create a processed embryo data set; performing specific gravity detection on the processed embryo data set to detect the weight of the at least one embryo; analyzing the at least one embryo to provide a comparative data set of the at least one embryo based on the embryo data sets; and classifying the at least one embryo as male or female, based on analyzing the at least one embryo.

In one aspect the sensor comprises one or more of a group consisting of: a camera, a laser, a photodetection sensor, a fiber optic sensor, a pyrometer, an infrared sensor, an electro-optical sensor, a through-beam sensor, a radiofrequency sensor, an ultrasound sensor, magnification device, and combinations thereof.

In one aspect of the device, the drop chamber lumen further comprises a continuous descent chamber open at both the proximal and distal portions capable of emptying into said recovery pool allowing a continuous fluid media for embryo descent and recovery. In another aspect the drop chamber lumen comprises a closed lower end capable of directing expulsion of the embryo from the lumen into a separate receptacle. In another aspect the drop chamber is transparent for visualization and timing of embryo descent through the lumen of the drop chamber. In yet another aspect, the drop chamber further comprises a designated timing zone or other timing mechanism for assessment of embryos. In another aspect the device comprises one or more drop chambers each depositing the multiple embryos into a separate recovery pool or receptacle to allow assessment of multiple embryos having unique identifications.

It is a further object of the present invention that the assessment is a non-invasive assessment of sex of an at least one embryo in the blastocyst stage without detrimental effects to the at least one embryo.

It is another object of the present invention to provide a method of non-invasive determination of the sex of a mammalian embryo, comprising: descending at least one embryo through a drop chamber comprising a lumen extending vertically from a media recovery pool; and assessing the at least one embryo by measuring the descending at least one embryo through said drop chamber, wherein said assessing step comprises measuring the estimated weight of the at least one embryo descending through a biocompatible media composition for determination of sex of the at least one embryo; and recovering the embryos from a recovery pool having fluid communication with the lumen of the drop chamber, wherein the recovery pool is capable of receiving embryos from the lumen of the drop chamber. In one aspect the assessing step further comprises making a quantitative assessment of the at least one embryo's weight, buoyancy, or density using specific gravity. In another aspect the assessing step comprises measuring the descending at least one embryo by any of a group consisting of: visual means, tagging, markers, computerized means, or combinations thereof.

In another aspect, the assessing step further comprises: capturing, by way of a sensor, data relating to the descent time of the at least one embryo obtained from measuring the descending at least one embryo; processing the data relating to the descent time of the at least one embryo to create a processed embryo data set; performing specific gravity detection on the processed embryo data set to detect the weight of the at least one embryo; analyzing the at least one embryo to provide a comparative data set of the at least one embryo based on the at least one embryo data sets; and classifying the at least one embryo as male or female, based on analyzing the at least one embryo.

In another aspect, the sensor for capturing data comprises one or more of a group consisting of: a camera, a laser, a photodetection sensor, a fiber optic sensor, a pyrometer, an infrared sensor, an electro-optical sensor, a through-beam sensor, a radiofrequency sensor, an ultrasound sensor, magnification device and combinations thereof.

The present invention is further capable of determining the sex of at least one embryo in the blastocyst stage without having detrimental effects on the embryo.

The present invention may further utilize one or more drop chambers, for determining the sex of more than one embryos, each of the one or more drop chambers capable of depositing the more than one embryos into one or more separate recovery pools to allow recovery of the more than one embryos following determination of the sex of the more than one embryos.

It is another object of the present invention to provide a computer-readable storage media storing instructions that are executable by a processor to cause a computer to execute operations comprising: capturing, by way of a sensor, data relating to the descent time of the at least one embryo obtained from measuring the descending at least one embryo; processing the data relating to the descent time of the at least one embryo to create a processed embryo data set; performing specific gravity detection on the processed embryo data set to detect the weight of the at least one embryo; analyzing the at least one embryo to provide a comparative data set of the at least one embryo based on the at least one embryo data sets; and classifying the at least one embryo as male or female, based on analyzing the at least one embryo.

In one aspect, the capturing step further comprises, capturing data relating to the descent time of the at least one embryo, said data generated from the sensor capable of observing each of the at least one embryo descending in the lumen of the drop chamber.

In another aspect, the sensor comprises one or more of a group consisting of: a camera, a laser, a photodetection sensor, a fiber optic sensor, a pyrometer, an infrared sensor, an electro-optical sensor, a through-beam sensor, a radiofrequency sensor, an ultrasound sensor, and combinations thereof.

In another aspect, processing the data relating to the descent time further comprises determining the applicable descent time of the at least one embryo. In another aspect, performing specific gravity detection further comprises calculating the specific gravity of each of the at least one embryo.

It is yet another object of the present invention to provide a system for determining the sex of a mammalian embryo comprising: inserting at least one embryo into a drop chamber comprising a lumen extending vertically, said drop chamber further comprising a growth supportive culture media composition; and descending said at least one embryo through said drop chamber; wherein said descent through said drop chamber allows for measurement of specific gravity of the embryo by descent time of the embryo through a biocompatible media, and wherein, the specific gravity measurement allows for determination of the applicable sex of the embryo.

In one aspect, the system further comprises one or more sensors designed to capture the descent time of the at least one embryo through the drop chamber. In another aspect, the one or more sensors comprises one or more of a group consisting of: a camera, a laser, a photodetection sensor, a fiber optic sensor, a pyrometer, an infrared sensor, an electro-optical sensor, a through-beam sensor, a radiofrequency sensor, an ultrasound sensor, magnification device and combinations thereof. In another aspect, the system comprises a computer-readable storage media storing instructions that are executable by a processor to cause a computer to execute operations comprising: capturing, by way of the sensor, data relating to the descent time of the at least one embryo obtained from measuring the descending at least one embryo;

processing the data relating to the descent time of the at least one embryo to create a processed embryo data set; performing specific gravity detection on the processed embryo data set to detect the weight of the at least one embryo; analyzing the at least one embryo to provide a comparative data set of the at least one embryo based on the at least one embryo data sets; and classifying the at least one embryo as male or female, based on analyzing the at least one embryo.

In another aspect, the system allows for recovery of the at least one embryo from a recovery pool following assessment of the sex of at least one embryo. In yet another aspect, the sensor comprises one or more of a group consisting of: a camera, a laser, a photodetection sensor, a fiber optic sensor, a pyrometer, an infrared sensor, an electro-optical sensor, a through-beam sensor, a radiofrequency sensor, an ultrasound sensor, magnification device and combinations thereof.

The system may further comprise utilizing one or more drop chambers, for assessing multiple embryos, each of the one or more drop chambers emptying into a unique recovery pool or specified area to allow determining the sex of multiple embryos having unique identifications. In another aspect the system is capable of utilizing one or more drop chambers, for assessing more than one embryos, each of the one or more drop chambers emptying into a unique recovery pool or specified area to allow determining the sex of more than one embryos having unique identifications.

BRIEF DESCRIPTION OF THE DRAWINGS

The foregoing and other objects, features, and advantages of the disclosure will be apparent from the following description of embodiments as illustrated in the accompanying drawings, in which reference characters refer to the same parts throughout the various views. The drawings are not necessarily to scale, emphasis instead being placed upon illustrating principles of the disclosure.

DETAILED DESCRIPTION

Figure 1A:
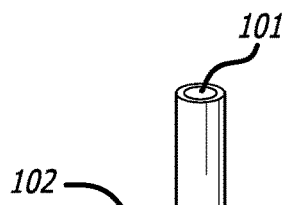
FIG. 1A depicts the device of the present invention as designed for use (note lid has been removed from diagram for ease of visualization).

While the making and using of various embodiments of the present invention are discussed in detail below, it should be appreciated that the present invention provides many applicable inventive concepts that can be embodied in a wide variety of specific contexts, goods, or services. The specific embodiments discussed herein are merely illustrative of specific ways to make and use the disclosure and do not delimit the scope of the disclosure.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

The present invention will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, devices, components, or systems. The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

Embryos start their life in the prenatal period of development of the mother as oogonia in primary or primordial follicles containing the early embryo surrounded by a single layer of granulosa cells in the parenchyma of the ovary. The number of follicles found in the ovary during this time period is the highest number the female will have in her entire life and will slowly decrease, mainly due to atresia, for the rest of her lifetime, until exhausted at menopause. During this developmental time period, the oogonia will begin the meiosis process and chromosomal rearrangements that will eventually lead to a genetically unique oocyte. This process will become quiescent during the dictate phase of prophase one and remain there until after birth. At a point in the future further development will begin again. At that time, the granulosa cells that surround the primordial follicle will begin to proliferate and create multiple layers around the oocyte (2-3), at this stage of development structure is called a secondary follicle. This can happen independently of a hormonal influence but further development will stall in the absence of the appropriate hormone cascade. In the presence of hormones a low percentage of follicles will eventually develop a large fluid filled cavity (antrum), 0.2-0.3 mm in rodents and 2-5 mm in humans, and be classified as tertiary follicles.

In humans under normal conditions, a single follicle will fully enlarge and ovulate (termed a graafian follicle) releasing the oocyte into the oviduct for potential fertilization. The ovulated oocyte is then caught by the infundibulum and moved into the oviduct for potential fertilization. At this stage of development the oocyte's anatomy has a nucleus, which has reactivated from the dictyate stage of prophase I and is continuing meiosis. The nucleus is housed within a large (>100-um diameter) cell surrounded by the vitelline membrane. Just beneath the membrane are collections of cortical granules. The vitelline membrane is surrounded by a periviteline space, which should contain the first set of cast off chromosomes; the first polar body. A protective protein shell called the zona pellucida surrounds the whole of the oocyte. In mammals, the zona pellucida is a barrier which acts to prevent more than one sperm from entering the oocyte, although it is common for multiple sperm to appear in the perivitelline space after fertilization. Under normal conditions, sperm cells will use enzymes such as esterase, acrosin, and neuraminidase released from its acrosomal region to cause a lysis of the zona pellucida allowing a path into the oocyte. The zona reaction is initiated when the head of the sperm cell fuses with the vitelline membrane. The cortical granules will then fuse with the vitelline membrane and empty their contents into the perivitelline space of the oocyte. This process by the cortical granules is what is thought to be responsible for the zona reaction. Once a sperm cell has successfully crossed the vitelline membrane, the zona pellucida will undergo the "zona reaction," a configurational change in its proteins, and the vitelline membrane will be modified to prevent sperm from penetrating, both events ensuring polyspermia (fertilization of an oocyte by more than one sperm) does not occur.

Once fusion of the oocyte and sperm's membranes complete the sperm cell's head and tail will travel in to the oocyte cytoplasm. The complete penetration of the sperm cell into the cytoplasm activates the second meiotic division of the oocyte, creating a second polar body and allowing for the nucleus to become the female pronucleus. The nucleus of the sperm cell begins to enlarge to form the male pronucleus as the sperm's tail degenerates. The presence of these two pronuclei demonstrates that a successful fertilization has occurred. The male and female pronuclei then will fuse into a single diploid aggregation of the chromosomes creating a zygote.

Once the process of fertilization is complete, the zygote will undergo cleavage. Cleavage is a process of mitotic cell divisions within the zona pellucida resulting in added cell numbers but no growth in size. The cells undergoing cleavage are called blastomeres. The initial one cell zygote will mitotically divide resulting in a two-cell (two blastomere) embryo. Then it will continue to divide creating a four, eight, sixteen-cell embryo and eventually enter into the uterus. With each blastomere division or cleavage, the resulting in smaller cells with less cytoplasm. At this stage the blastomeres begin to tightly align themselves with one another increasing cell-to-cell adhesion, creating a structured complex referred to as a morula. The morula will continue to compact with gap junctions forming between the interior cells and tight gap junctions forming between the cells on the exterior of the embryo. During the next few days fluid from the uterus will begin to seep into the embryo creating a fluid filled cavity called a blastocele. As the cavity fills with more fluid, the individual blastomeres are pushed outward onto the inner lining of the zona pellucida creating a blastocyst. Some differentiation occurs with the cells, some will become the outer cell mass that lines the epithelial wall called a trophoblast, which will become the placenta, and some will group together at the polar end of the blastocyst forming an inner cell mass or embryoblast, which will become the embryo. As the blastocyst expands and grows it will press against the zona pellucida. This pressure, coupled with the release of proteolytic enzymes from the blastomeres, will cause the zona to thin and eventually break, allowing the embryo to be released. This is termed hatching. After the blastocyst has hatched, the trophoblast will associate and establish a relationship with the uterus and implant to gain the necessary source of nutrients for growth.

Assisted Reproductive Technologies (ARTs) have made significant improvements over the last thirty years. Improvements in management protocols, culture technique, and culture media have helped increase pregnancy rates while simultaneously decreasing the number of embryos transferred. Programs which once measured success rates in terms of the occasional pregnancy now routinely report annual success rates 40%-60%. The ultimate goal of all ART programs should be to move toward single embryo transfers while maintaining high pregnancy rates. Invasive procedures, even while increasing pregnancy rates, are also linked to increasing miscarriage rates. Given the cost of the procedures, risks associated with medications and surgical procedures, and the emotional toll negative pregnancy results have on the couple; any improvement in embryo selection which is non-invasive, less subjective and leads to higher pregnancy rates, while limiting the risk of multiple gestations would represent a significant improvement in women's reproductive health.

Pre-implantation genetic testing (PGT) has proven an effective method for embryo sexing. There are also several techniques known in the art which are capable of providing sexing of embryos, including invasive methods and non-invasive methods.

Invasive embryo sexing methods include, inter alia: (i) karyotyping, (ii) sex chromatin identification, (iii) Y-specific DNA probes, and (iv) polymerase chain reaction (PCR) method.

Karyotyping is an invasive method of determining sex of an embryo wherein some cells are removed from an embryo and cultured with colchicine that cause the cells to cease dividing (mitosis). The cells are then lysed and stained for observation of X or Y chromosomes. The method is inexpensive, but the techniques are capable of causing substantial harm to the embryo, and further requires trained personnel and can take 12 hours or more to perform.

Identifying sex chromatin is another way of determining sex of an embryo. This invasive method focuses on identifying a Barr body, resulting from the inactivation of one of the two X-chromosomes present in female cells. Cells from female embryos are therefore expected to show Barr bodies. However, this technique is not capable for sexing all types of mammals, due to the consistency of the chromatin. Further, all cells may not have the Barr bodies present, leading to false diagnosis. Further, large amounts of cells are needed, resulting in potential damage to the embryo.

Y-specific DNA probe techniques are another invasive technique, involving obtaining several cells from an embryo, exposing the DNA and hybridizing with a Y-chromosome-specific probe, thus allowing for detection of male embryos. While effective and highly accurate, this process remains invasive, and is expensive and time consuming.

The PCR method allows for amplification of Y-chromosome-specific DNA and is the most reliable and commonly used method of sexing embryos. The method involves removal of a small number of cells (typically not traumatic to the embryo) and is sensitive, accurate and reliable. However, as with other techniques, the process requires technical skill and is time consuming.

The above procedures are nonetheless considered invasive, not without risks, and can sometimes lead to erroneous results. It is also time consuming and requires a significant investment in equipment. Numerous groups have been searching for a non-invasive means of improving embryo sexing. However, to date, little progress has been made in finding an alternative to traditional morphology alone or morphology coupled with the above techniques, particularly the PCR method.

Available non-invasive embryo sexing methods include, inter alia: (i) detection of X-linked enzymes, (ii) metabolomics assessment; and (iii) detection of H-Y antigens.

Using the detection of X-linked enzymes, the embryo is not subjected to any harm or manipulation during the testing procedure, thus being considered non-invasive. The presence of two X chromosomes in a female embryo presents an increase in enzymes glucose-6-phosphate dehydrogenase (G6PD), Phosphoglycerate kinase, A-galactosidase, and Hypoxanthine guanine phosphoribosyl transferase (HPRT). Such enzymes are then tested in embryos, suggesting that a female embryo will present higher concentrations than a male embryo. However, there are limitations to this approach, in that embryo viability is reduced, partially due to the time the embryo is required to be measured using this method.

Metabolomic profiling is another non-invasive technique using optical and non-optical spectroscopies, where key aspects of surplus culture media are analyzed, but reliability and bias consistencies often result in inaccurate results.

In using the detection of H-Y antigens, embryos are incubated for a period of time (30-60 minutes) with antibodies and then an additional period of time (30-60 minutes) with an antibody containing a fluorescent dye. H-Y positive males fluoresce while H-Y negative females do not fluoresce. The H-Y method is capable of use with most mammalian species and have a high success rate (approximately 85%). However, the embryo must remain in this process for a long period of time. The technique is also considered invasive as the dye is considered mildly toxic. Further, reagents and equipment requirements are often significant and expensive.

It is therefore an embodiment of the present disclosure to provide a device and related system and method, for non-invasive determination of the sex of an embryo based on specific gravity. It has been determined that, based on differences in the size of chromosomes between males and females, female embryos will weight slightly more than male embryos. The difference is miniscule but indeed detectable using the embodiments set forth herein. Currently, preimplantation genetic testing can offer insights into the whether children will have genetic abnormalities and the sex of the embryo; however this technique is very invasive and requires the highly skilled individuals using expensive instruments. With this new adaptation of the previously disclosed apparatus, prospective parent might now be able to choose the sex of their child, and livestock producers will be able select the preferred sex based on their needs.

In a blastocyst there are around 300 cells, each having an XX or XY chromosome pairing. There is an very small weight differential between the X and Y chromosomes, and when multiplied by the number of cells (n=300), a detectable difference is possible. This principle only applied to embryos within one standard deviation of the mean and can only be reflective between embryos from the same mother.

In one example, an observation of large numbers of blastocyst stage embryos occurred, wherein 169 mouse embryos were dropped through the system of the present invention. The blastocysts were expected to cluster on the mean, but it was observed that while the healthy embryos' descent time cluster around a mean and the overall pattern is the previously described bell shaped curve, the absolute peak of the curve is actually bifurcated with two distinct clusters on either side of the established mean with less than 2% of the embryos having descent time in the gaps between the two clusters.

Advancement in all aspects of ART has improved the technique to the point where both researchers and lawmakers are calling for single embryo transfer to become the norm. The device of the present invention, by itself, or in combination with other techniques, might represent a step forward in determining individual embryo sex and thus embryo selection for SET.

It is therefore an embodiment of the present invention to provide a system for the non-invasive sexing of early stage embryos (pre-hatching) based upon specific gravity, density and/or estimated weight. In one embodiment the system allows 100% recovery of embryos and can detect sex at the earliest stages of development. Estimation of embryo density is a non-invasive, objective way of determining sex of the embryo. Estimation of embryo lipid content/biochemical content is obtained by a specific gravity technique, which has been a common means of estimating lipid content in live individuals or food products. Specific gravity determination involves water displacement that helps determine the density of the embryo. As differences in weights of objects of equal size are based solely on density, the density of the embryo at this stage of development must be an estimation of weight. Therefore, estimating the embryo weight leads to further estimation of embryo sex selection of viable embryos for ART applications. Further, while the examples herein primarily address in vivo-produced embryos, the present invention is applicable to IVF and flushed embryos as well.

The study of flow chemistry is the study of chemical reaction in a flowing stream instead of a static batch production. A micro fluidic device can be described as drop chamber—a tube or channel that has either a constant flow of some fluid streaming through it at a certain velocity. A segmented flow system where there is gaseous bubbles or solvent spacers to separate specific reactions or materials from one another can be used as well. Such systems have been proven to have many benefits such as an excellent heat and mass transfer capability, allowing for tight temperature control at exponentially high or low temperatures for increased reaction rates. Microfluidic devices have also shown to have elastic instabilities that allow for induced diffusion between whatever fluid is in the device and the particle, reaction or material traveling through it.

In one embodiment the present invention presents a specific gravity means of assessing embryo weight, and thus sexing of said embryo. While not a true microfluidic environment, in that the embryo travels through the fluid rather than fluid flowing over the embryo, presenting microfluidic effects on the embryo as it descends through the specific gravity chamber.

In another embodiment, the system is composed of a drop chamber, referred to as the drop chamber, extending into to a collection pool, referred to also as the collection pool, to allow for recovery of embryos. In a further embodiment, the system contains, and is operated using, an embryo culture media of users choosing and compatible with embryo survival outside of controlled culture conditions. In an even further embodiment, the system contains, and is operated using, an embryo culture which is a growth supportive embryo culture media (i.e. culture media which actually enhances embryo growth).

In yet another embodiment, the system contains a pressure seal to allow the media to be continuous from the top of the drop chamber to collection pool. The system has a "timing zone" to determine the descent time of the embryo over a known distance. The timing zone may be designated by marks, etching, pigments or inks, or other methods to designate the upper and lower boundaries of the timing zones. The drop chamber which comprises the lumen acting as the drop chamber is preferably transparent, or is comprised of sections related to the applicable timing zone to allow for detection and assessment of the descent of the embryo of interest. In a further embodiment, assessment means any observation or evaluation through visual means or by other means of detecting the movement downward of the embryo of interest, including assessment by tagging, markers, or by computerized means utilizing a processor having programmable logic designed to detect the embryo of interest during descent through the timing zone.

In a further embodiment the system drains media from the drop chamber into the recovery collection pool upon breaking of the pressure seal to ensure flushing of the embryo into the recovery collection pool, thus creating fluid communication between the lumen of the drop chamber and the collection pool. It is a preferred embodiment of the present invention that said system potentially increases the embryo growth rate over static culture.

In yet another embodiment, the system has an optional rotating, revolving, carousel, or otherwise multiple-welled or multiple-strawed configuration, allowing for the ability of the drop chamber to have multiple chambers, each having its own recovery pool, or collection pool to allow collection of information about individual embryos. In another embodiment, a single drop chamber is positioned at various times over multiple recovery pools to allow collection of information about individual embryos while allowing a single chamber's use.

Turning to the figures of the present invention, various aspects are described. Other configurations, such as a square rather than round drop chamber or different collection pool might be employed without chaining the functionality of the device. FIG. 1A depicts the specific gravity system as designed for use (note lid has been removed from diagram for ease of visualization). A drop chamber 102 is positioned above a collection pool or reservoir 104. The outer diameter of the drop chamber 102 allows for monitoring of the inner lumen 101 which acts as a descent chamber of the drop chamber 102. Culture media which is biocompatible is maintained in the inner lumen 101, as well as in the collection pool 103. The drop chamber 102 is positioned vertically over the collection pool 103 in order for the lower end of the drop chamber 105 to allow fluid communication to exist between the lumen 101 of the drop chamber 102 and the collection pool 103. An outer surface of the collection pool 104 is designed to contain the culture media. The configuration of the collection pool may be cylindrical, rectangular, or any shape necessary for compatibility with surrounding equipment and instrumentation. An embryo is placed at the top of the open end of the drop chamber, the lumen 101 representing a specific gravity chamber and allowed to sink through the media. The embryo is then subjected to assessment. In one embodiment, the embryo's rate of descent is measured as it passes through a marked, or otherwise distinguishable, section of the drop chamber labeled the "timing zone." For example, the timing zone may be 10 cm in the length or less. In one embodiment, the timing zone is 5 cm. In another embodiment, the timing zone is 2 cm. In a preferred embodiment the timing zone is 1 cm. Once the timing is completed the embryo continues to descend into the middle section of a collection pool, which may represent a standard organ culture dish or other reservoir capable of receiving the embryo within the culture media, which may be biocompatible in one embodiment, and growth supportive in another embodiment.

Figure 1A:
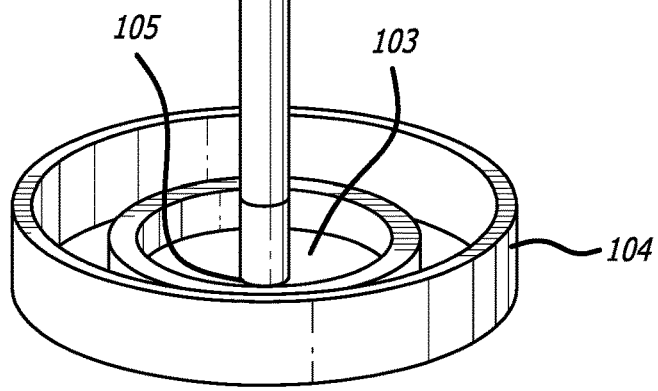
Figure 1B:
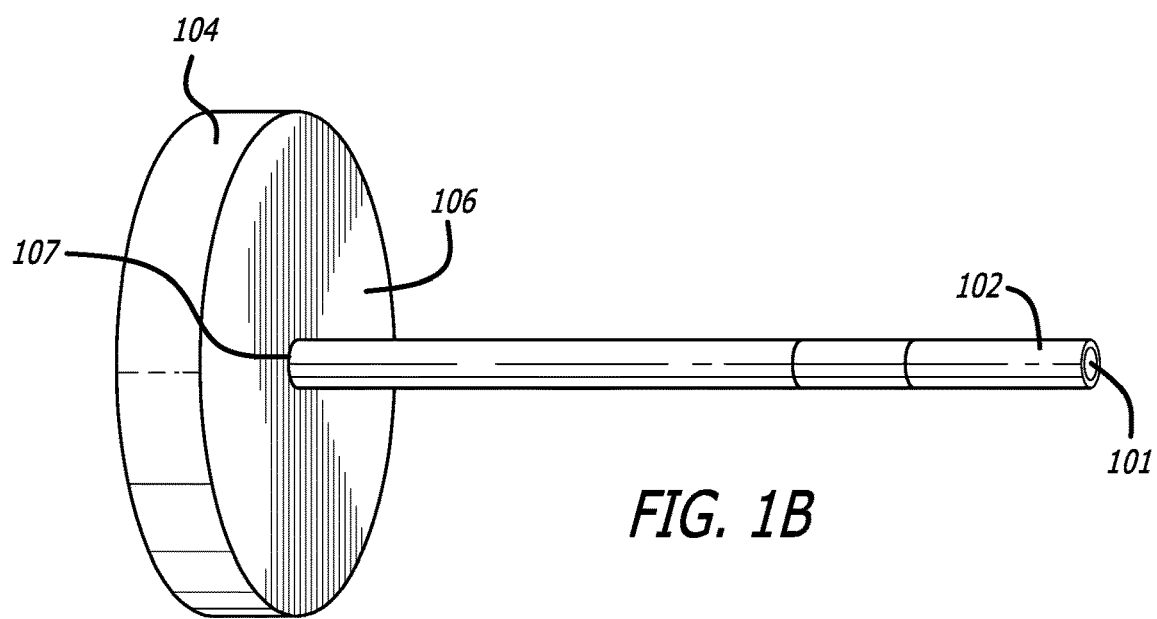
FIG. 1B depicts the device of the present invention in a form factor having a removable lid configuration and positioned horizontally.

Turning to FIG. 1B, a representative device of the present invention is shown with a lid configuration 106 and positioned horizontally, which is non-functional in terms of performing assessments of embryos. The lid 106 allows for protection and pressurization of the inner collection pool housed by the outer portion of the collection pool 104. The lumen 101 is presented within the drop chamber 102, which extends distally from the collection pool 104. An aperture 107 in the lid 106 is capable of receiving the drop chamber 102 for purposes of insertion into the collection pool 104 and achievement of fluid communication between the lumen 101 and the inner collection pool 104. For the purposes of the present invention the device must be positioned vertically for the assessment to occur, as the descent of an embryo may be affected by positioning the drop chamber 102 in any position that is not vertical. The lid 106 can then be removed for easy embryo recovery and return to culture.

Figure 2:
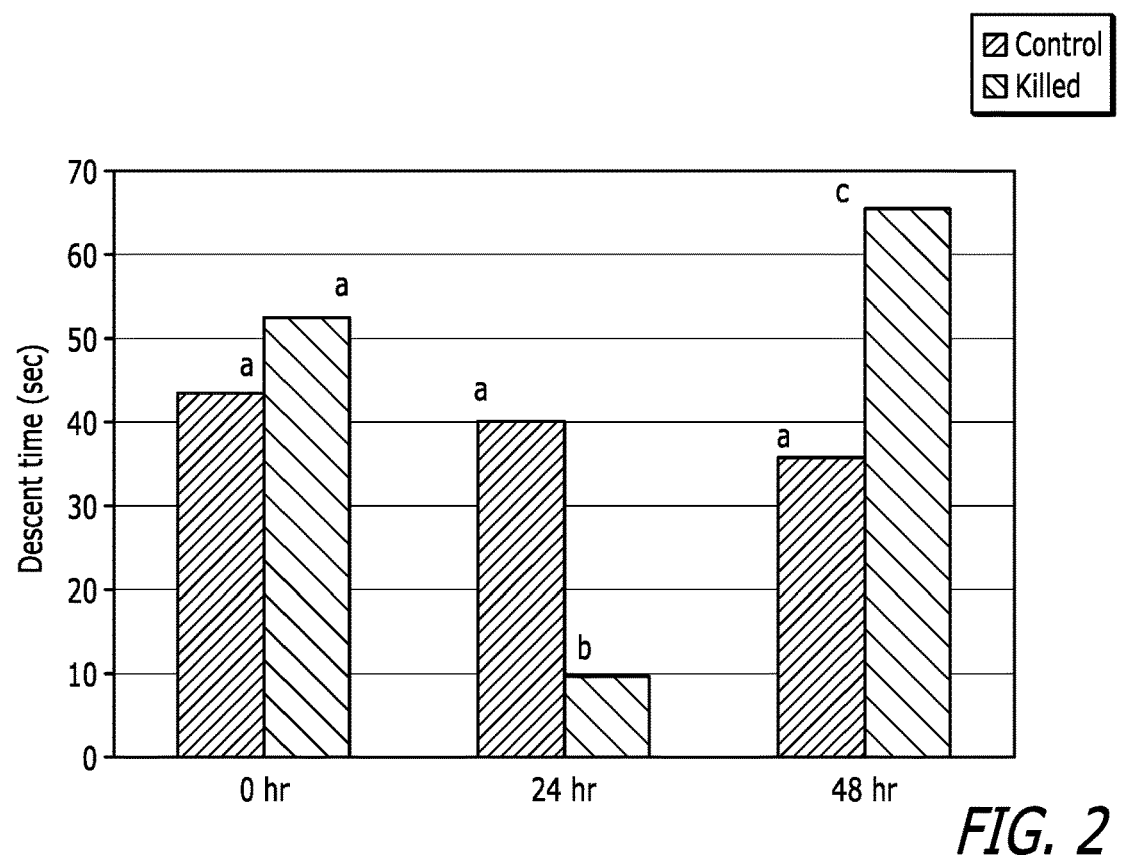
FIG. 2 depicts a comparison of the descent time of control (non-heat exposed) and heat-killed embryos through the system of the present invention at 24 hour intervals over a two day period.

FIG. 2 presents a comparison of the descent time of control (non-heat exposed) and heat-killed embryos through the device of the present invention at 24-hour intervals over a two-day period. While the control embryos demonstrated patterns similar to those reported in previous studies, heat-killed embryos exhibited drastically different patterns of descent. The expectation that the differing patterns of descent are attributable to changes in membrane integrity ($P<0.001$).

Figure 3:
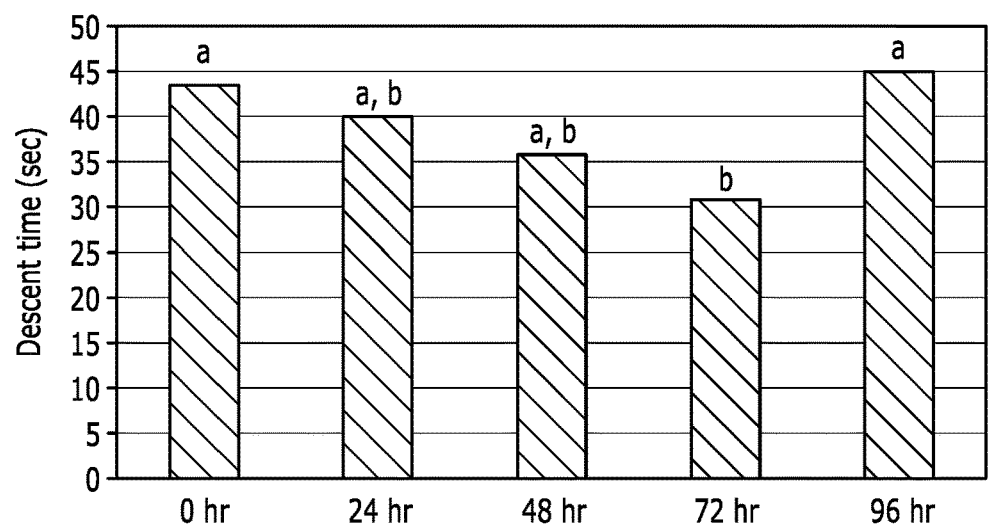
FIG. 3 depicts descent time of control (non-heat exposed) embryos over a five day period through the system of the present invention.

FIG. 3 presents the descent time within the device of the present invention of control (non-heat exposed) embryos over a five-day period. Note changes in descent time appear to be affected by increases in embryo cell number as embryos continue to grow over time (time 0 hour—one cell stage, 96 hours—blastocyst). Bars with different letters indicate a difference between measurement times ($P<0.02$).

Figure 4:
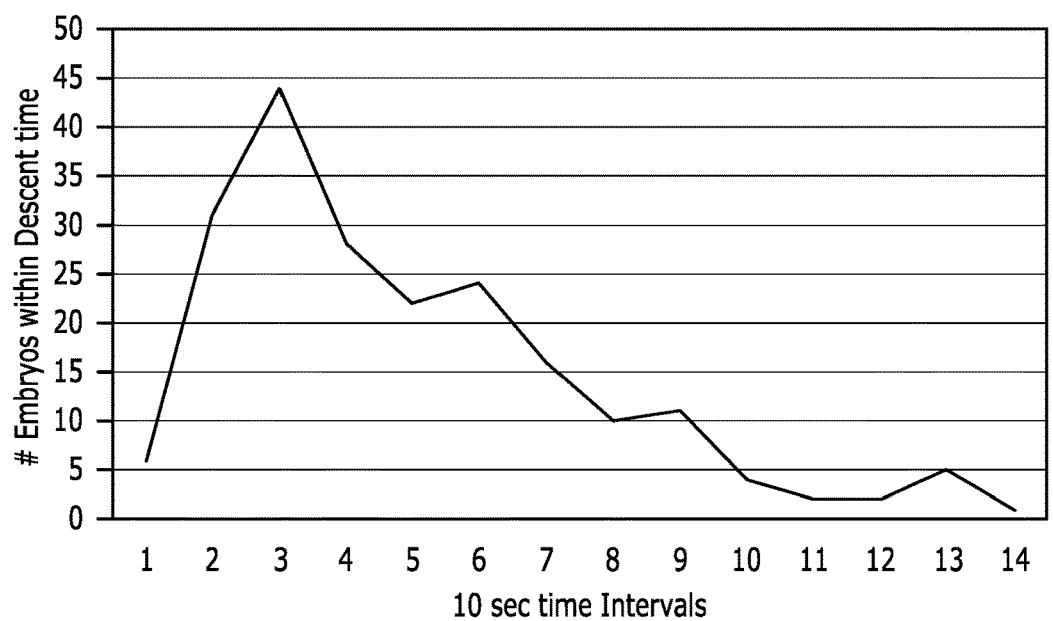
FIG. 4 depicts a comparison of the descent times of 207 one-cell embryos from 27 donor animals "suspended" through the system of the present invention.

FIG. 4 presents a comparison of the descent times of 207 one-cell embryos from 27 donor animals "dropped" through a the device of the present invention, which acts as a modified specific gravity chamber. While descent times ranged from 10-140 seconds, >70% of the embryos was clustered +20 seconds of the population mean. Furthermore, the data for individual embryos suggest a skewing towards faster descent times, attributable in part to the influence of maternal body composition.

Figure 5:
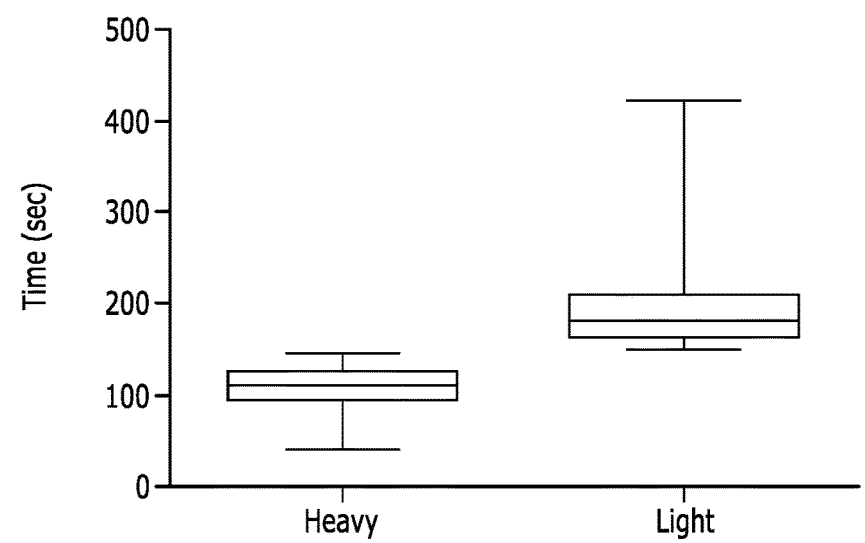
FIG. 5 depicts the mean decent times of two populations of blastocyst stage embryos that cluster on either side of the arithmetic mean (N=160).

FIG. 5 presents data from 160 embryos demonstrating the two clusters formed on either side of the arithmetic mean. Ratios established are approximately 49 verses 51% or the same rations seen at birth of female to male offspring.

Figure 6:
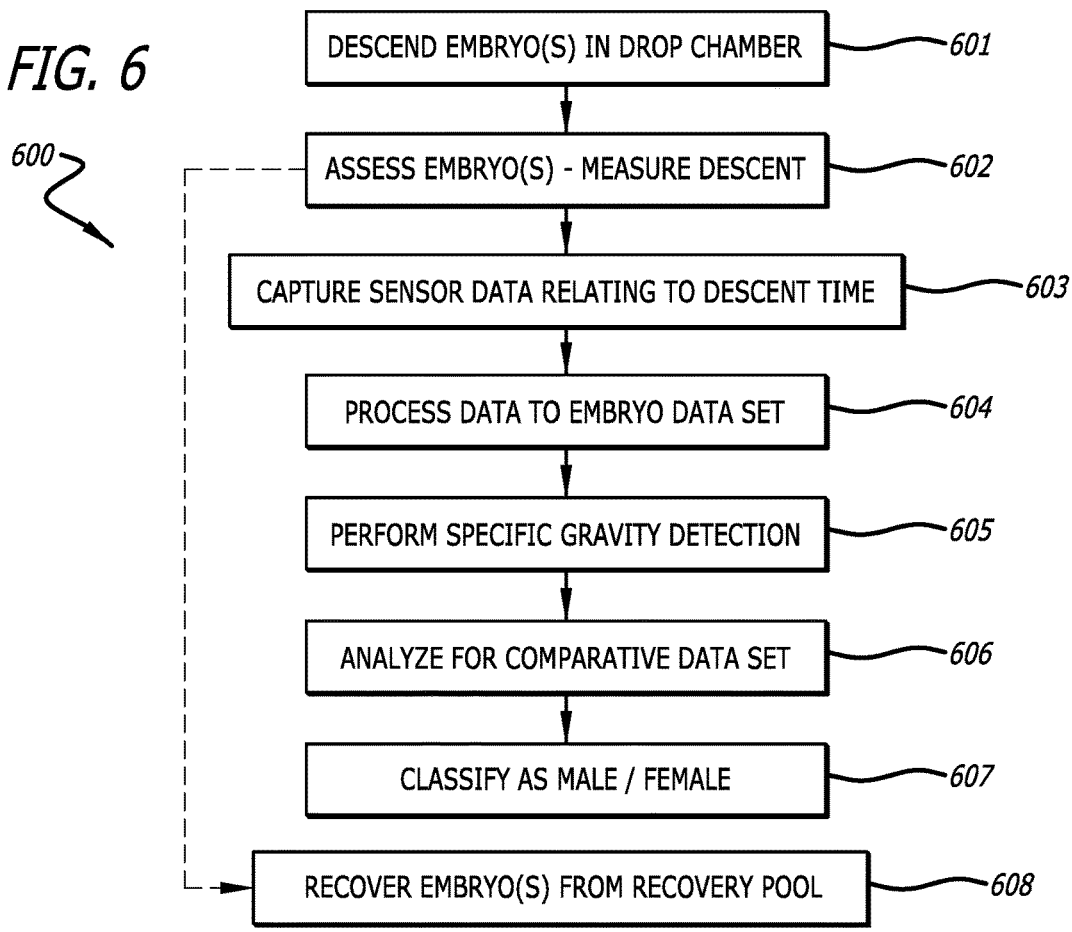
FIG. 6 depicts a flow diagram of the method of one embodiment of the present invention.

FIG. 6 presents a flow diagram of an exemplary method of determining embryo sex in accordance with an example embodiment. The method 600 is provided by way of example, as there are multiple means for carrying out the method 600 within present invention. The embodiments described herein and in the Figures are capable of carrying out the method 600, and the illustrated order of the method 600 are capable of being performed in different order than is presented in FIG. 6.

A descent step 601 is performed by placing the at least one embryo in a drop chamber comprising a lumen. Within the lumen, a biocompatible culture media is utilized. The embryos are able to descend within the media. An assessment step 602 is capable of measuring the descent of the at least one embryo through the lumen of the drop chamber. Such assessment step 602 is capable of being performed by a variety of sensing techniques which may include visual assessment to sensors capable of automated assessment and classification, such as: a camera, a laser, a photodetection sensor, a fiber optic sensor, a pyrometer, an infrared sensor, an electro-optical sensor, a through-beam sensor, a radiofrequency sensor, an ultrasound sensor, magnification device and combinations thereof. When using a sensor, a capturing step 603 is performed to capture sensor data relating to the descent time. Such data is provided to a processor capable of performing processing step 604 to create an embryo data set. This data set may further include other embryo characteristics, including but not limited to, embryo diameter, embryo cell count, orientation, and the like. Following the processing step 604, detection step 605 is performed to provide specific gravity detection on the processed embryo data set to detect the weight of the at least one embryo. An analyzing step 606 is then performed to analyze the at least one embryo to provide a comparative data set of the at least one embryo based on the embryo data set. A classification step 607 is the performed to classify the at least one embryo as male or female, based on analyzing the at least one embryo. This classification step 607 may then be presented as male or female embryos based on the analyzed data set. Following the assessment of the at least one embryo, the embryos are capable of being recovered from the recovery pool via a recovery step 608. The recovery step 608 may be performed at a future date following storage. The recovered embryos are then capable of being utilized based on the non-invasive nature of the method of the present invention. In another embodiment, the at least one embryo may be kept in the lumen of the drop chamber for storage and transport. Storage may include cryopreservation in traditional storage containers. In another embodiment the drop chamber is in fluid communication with one or more recovery pools or receptacles, which are further capable of being sealed and/or configured for removal and transport to a desired location. As with the processed sensor data, a processor may further be capable of actuating one or more valves or gating assemblies to direct the at least one embryo into the one or more recovery pools, thus providing a sorting feature.

In another embodiment, the system of the present invention is capable of determining embryo properties such as development potential, viability, survival following cryopreservation, defects such as trisomy or aneuploidy, and the like. This may further included additional embryo data such as cell count and diameter. These data are further capable of being combined with the sensor data to further increase accuracy or to establish comparative data/thresholds.

Figure 7:
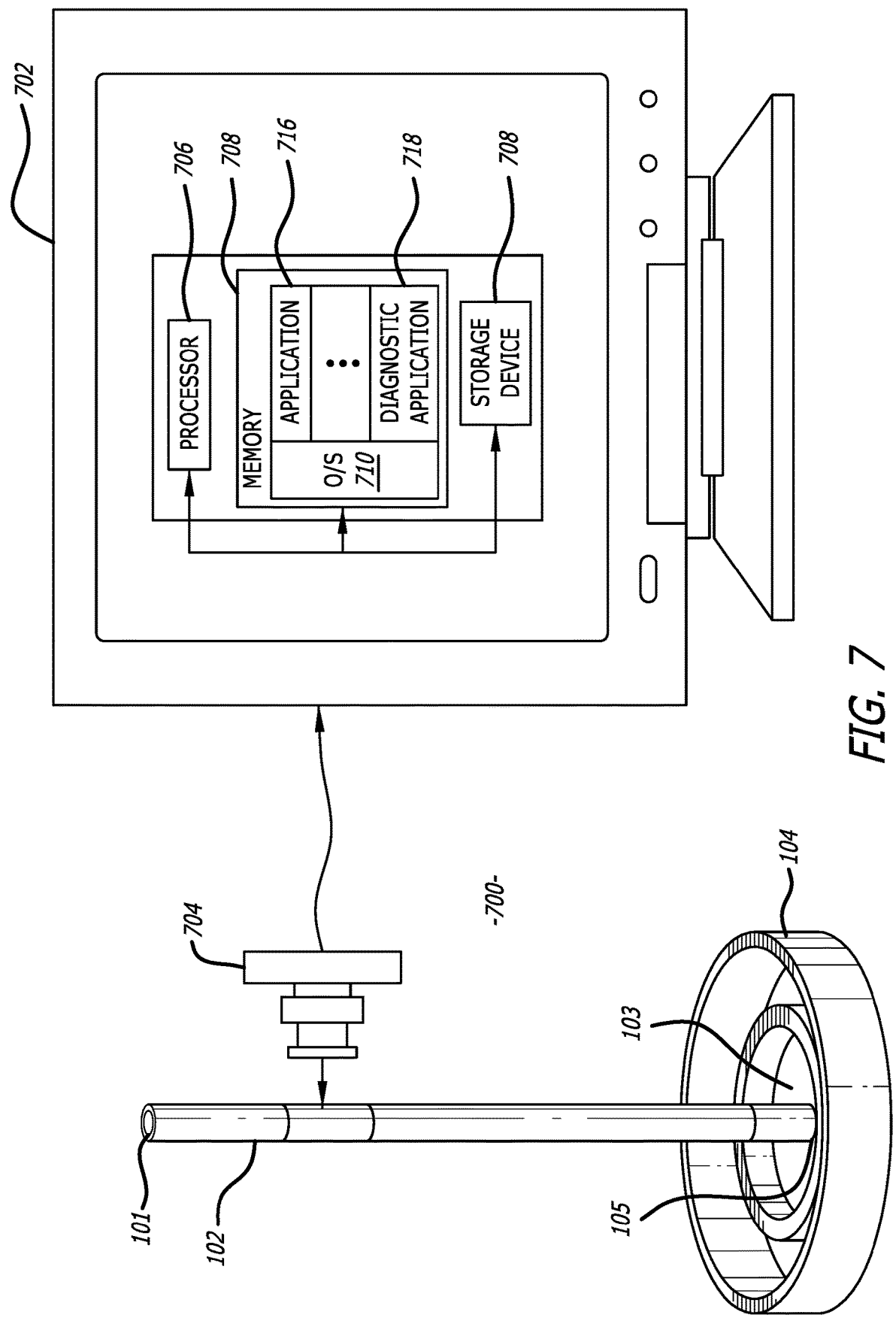
FIG. 7 depicts the device of the present invention with automated measurement.

FIG. 7 presents the device 702 which can include at least one processor 106, at least one memory 708, and at least one storage device 708. According to some embodiments, the device 702 can represent any form of a computing device, e.g., a smartphone, a tablet, a laptop, and a desktop computing device.

According to some embodiments, the processor 706 can be configured to operate in conjunction with, the memory 708 and the storage device 708, to enable the device 702 to implement the various techniques to detect embryo sex by measuring the drop times of at least one embryo through the lumen of a drop chamber. According to some embodiments, the storage device 708 can represent a storage device that is accessible to the device 702, e.g., a hard drive, a solid-state drive (SSD), a mass storage device, and a remote storage device.

In some embodiments, the storage device 708 is a storage device internal to the device 702. The storage device 708 can be configured to store an operating system (OS) file system volume that is mounted at the device 702, where the OS file system volume includes an OS 710 that is compatible with the device 702. Examples of the OS 710, specifically where the device 702 is a smartphone includes Google Android®, Research in Motion's BlackBerry OS, Microsoft's Windows Phone® OS, and Apple iOS®.

Still referring to FIG. 7, the OS 710 enables a variety of processes to execute on the device 702, e.g., OS daemons, native OS applications (e.g., application 716), native OS applications, user applications, and the like. For example, the application 716 can be a photo application, a mail application, a camera application, and a contacts application.

Additionally, the OS 710 enables the diagnostic application 718 to execute on the device 702.

The raw specimen can be captured by one or more applications executing on the device 702, such as a camera application or the diagnostic application 718. For example, the raw specimen can be captured using a camera application native to the OS 710 or separately installed from an application store. In one embodiment, the raw specimen is captured by the camera application and sent to diagnostic application 718. In other embodiments, the diagnostic application 718 is configured to render for display a graphical user interface capable of displaying observed characteristics of at least one embryo and its descent and/or weight characteristics observes by the sensor 701. The sensor 701 may be a camera, a laser, photodetection sensor, fiber optic sensor, pyrometer, infrared sensor, electro-optical sensor, through-beam sensor, radiofrequency sensor, ultrasound, and the like.

Figure 8:
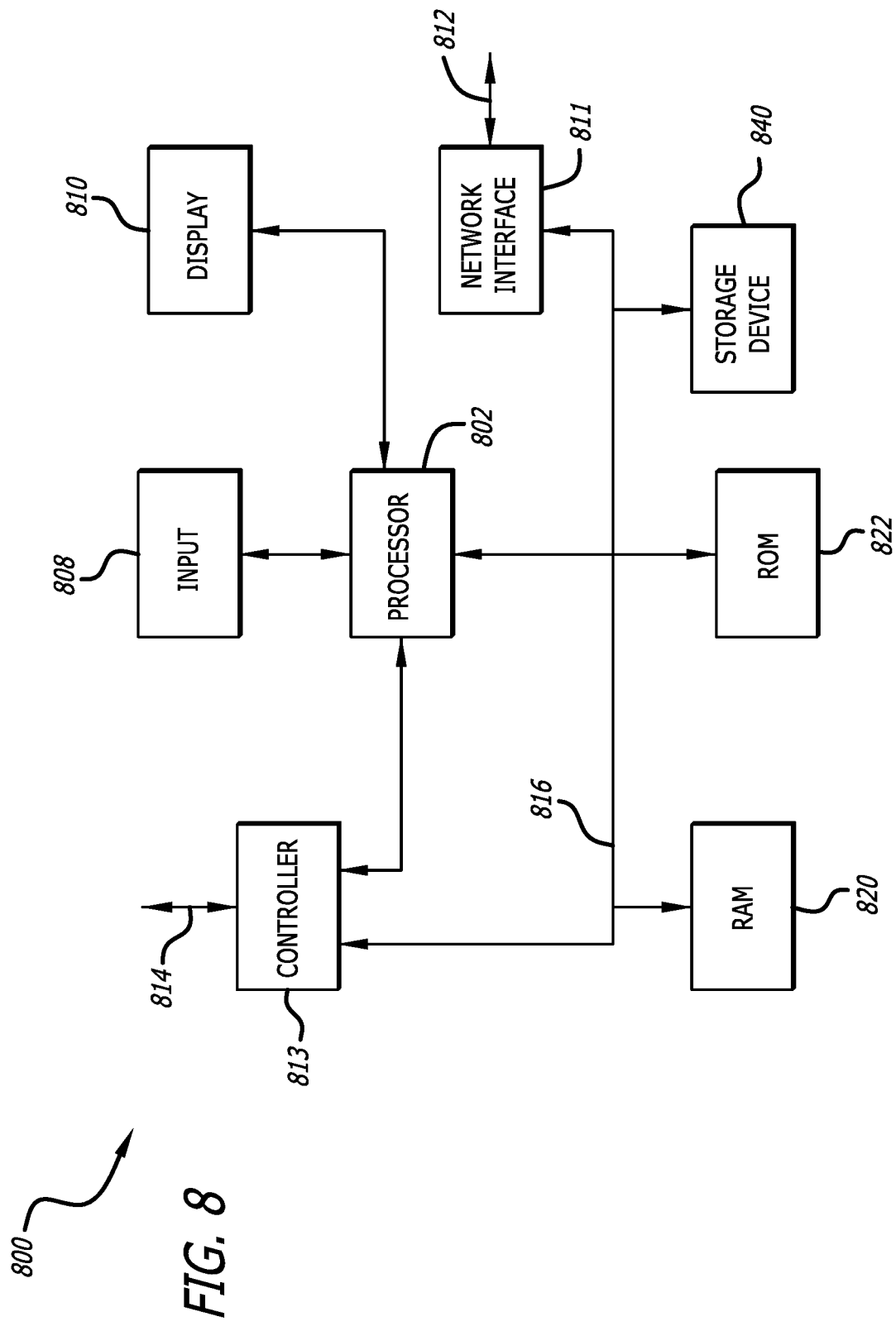
FIG. 8 depicts a detailed view of a computing device of the present invention for automated measurement of embryo descent.

FIG. 8 illustrates a detailed view of a computing device 800 that can represent the device of FIG. 1 used to implement the various techniques described herein, according to some embodiments. As shown in FIG. 8, the computing device 800 can include a processor 802 that represents a microprocessor or controller for controlling the overall operation of the computing device 800. The computing device 800 can also include a user input device 808 that allows a user of the computing device 800 to interact with the computing device 800. For example, the user input device 808 can take a variety of forms, such as a button, keypad, dial, touch screen, audio input interface, visual/image capture input interface, input in the form of sensor data, and so on. In an exemplary embodiment, the user input device 808 can be an optical sensor or laser sensor capable of observing the drop of at least one embryo through the lumen of a drop chamber. Still further, the computing device 800 can include a display 810 that can be controlled by the processor 802 (e.g., via a graphics component) to display information to the user (e.g., display a raw or processed specimen). A data bus 816 can facilitate data transfer between at least a storage device 840, the processor 802, and a controller 813. The controller 813 can be used to interface with and control different equipment through an equipment control bus 814. The computing device 800 can also include a network/bus interface 811 that couples to a data link 812. In the case of a wireless connection, the network/bus interface 811 can include a wireless transceiver.

As noted above, the computing device 800 also includes the storage device 840, which can comprise a single disk or a collection of disks (e.g., hard drives). In some embodiments, storage device 840 can include flash memory, semiconductor (solid state) memory or the like. The computing device 800 can also include a Random-Access Memory (RAM) 820 and a Read-Only Memory (ROM) 822. The ROM 822 can store programs, utilities or processes to be executed in a non-volatile manner. The RAM 820 can provide volatile data storage, and stores instructions related to the operation of applications executing on the computing device 800.

Those skilled in the art will recognize that the methods and systems of the present invention may be implemented in many manners and as such are not to be limited by the foregoing exemplary embodiments and examples. Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

The examples below provide illustrative embodiments of the present invention. While various embodiments have been described for purposes of this disclosure, such embodiments should not be deemed to limit the teaching of this disclosure to those embodiments. Various changes and modifications may be made to the elements and operations described above to obtain a result that remains within the scope of the systems and processes described in this disclosure.

EXAMPLE 1: Design of Specific Gravity Chamber for System

Initial studies were conducted using 0.5 mL straws filled completely with media. The media-filled straw, serving as the drop chamber, was positioned perpendicular to the ground such that the open end was at the top and embryos were placed at the meniscus and allowed to descend in response to gravity while being observed through a dissecting microscope. While it is recognized that specific gravity techniques measure density, in cases where the object's shape and size are equal density is a very close estimation of weight. Therefore, by measuring the descent time of the embryos over a set distance and comparing it to the descent time of beads of a similar size and shape to embryos, and with a known density and diameter of the beads, a mathematical formula was derived making it possible to estimate embryo weight as shown in more detail below.

The system of the present invention allows the embryo to complete its descent into the central well of an organ culture dish. The lid of the dish is modified to accommodate the descent chamber, by providing an aperture in the lid for insertion of the drop chamber, and is also equipped with a pressure seal to maintain the fluid levels within the descent chamber during use. Prior to testing embryos, the established mathematical formula was verified using previous experiments with bead controls. One hundred percent of the beads were recovered in the lower central well. Once the standard curve was re-established, a series of one-cell embryos (N=35) were collected from 4 mice (CB6F1 mice; Charles Rivers, Burlington, Mass.) previously stimulated using standard protocols, were run through the chamber to test recovery. It was found that most embryos were automatically located in the lower central well. It was also found that the few embryos that adhered to the wall of the descent chamber could be rinsed into the central well and 100% of embryos "dropped" through the system were recovered. Embryos were then placed in culture to determine whether they would continue development for a minimum of two division cycles.

It is well established that living cells are dependent on their semi-permeable membranes to establish the chemistry necessary to sustain life. The destruction of the semi-permeable properties of the membrane would cause leakage of cellular components, changes in intracellular chemistry and, therefore, in theory, a significant shift in cellular weight as water shifts into and out of the cells. Using this approach, the device of the present invention is capable of detecting differences between living and dead embryos based on changes in embryo's specific gravity after death. To prove this hypothesis, embryos were collected from a series of 5 mice (N=79) after hyperstimulation. The embryos from each mouse were split equally between two treatments. The first group of embryos (N=39) were weighed and then placed into standard culture using 10% serum and a Ham's F-10 media (Irvine Scientific; Santa Ana, Calif.) for a period of 48 hrs. The second group of embryos (N=39) were also weighed to insure consistency with the first group's initial assessment, but then killed by placing their culture dish on a 60° C. hotplate for 30 minutes. Once heat killed, these embryos were placed under the same culture conditions as the controls. All embryos were re-weighed using the device of the present invention after 24 and 48 hrs in culture and controls weighed every 24 hrs after until 120 hours (see FIG. 2).

As described above, it is recognized that specific gravity is a measure of density, not weight. However, if the shape and size of the objects being measured are held constant, then density can estimate weight. Given the consistent size and shape of most non-expanded embryos (zygote to early blastocyst stage) the device of the present invention should provide an estimation of weight. Initial studies show the device of the present invention containing a collection pool within a chamber not only demonstrated 100% recovery of embryos, but also that the recovered embryos continued to develop at normal rates through 2-4 division cycles. Further, as the chamber media had not changed and repeated measurement of the descent times of the control borosilicate glass beads (data not shown) were similar to measurements performed in the previous chamber, the same curve could be used to estimate embryo weight. As suggested by previous work, it appeared buoyancy might be a useful tool in predicting embryo growth and justified future investigation of early embryo weight's relationship with embryonic development. However, upon performing a viability study with mouse blastocysts, data points were placed on a scatter plot just to visualize measurements obtained. Upon observing the cluster, it was observed that there were 2 concentrated clusters rather than 1. Further, the 2 clusters each contained 50% of the data points rather than a cluster of outliers. See FIG. 5. The result was 2 equal groups, suggesting that the clusters represented a male and female cluster. From general knowledge that general animal populations are approximately 50% male and 50% female (51% male and 49% female typically). Further, it is well established that the X chromosome is larger and heavier than the Y chromosome.

To confirm this, the system of the present invention 600 bovine embryos were tested, and PCR was additionally used to determine the sex of the embryos. In measuring descent times of embryos in the blastocyst stage, it was observed that the embryos possessed an outline of perimeter cells (trophoblast), a lump of cells inside this perimeter (inner cell mass/embryoblast aka developing fetus) and a hollow empty cavity (blastocoele). Interestingly, every embryo dropped lead with the inner cell mass during descent. This 'head first' orientation means the heaviest part of the embryo actually fell first with the blastocoele parachuting on top of it. As a larger, more expanded embryo has more drag and resistance in the biocompatible media the system accounts for embryo diameter in analyzing the at least one embryo. This observation further supports that the measurement of embryo specific gravity/buoyancy is due a considerable mass driving the embryos rate of decent. This unexpected observation allows for all individual embryos to descend in the same orientation even though they are such small organisms. Therefore, X chromosome weight compared to Y chromosome weight can make a difference in the embryos descent time. For example, cattle have 60 chromosomes meaning the X or Y chromosome are just 1/60 of the total chromosome number. Further chromosomes are but a small component in a cell along with proteins, lipid, water, salts, substrates etc. This low percentage of total cellular composition would seemingly not affect embryo buoyancy which could be detected in the measured descent time within the drop chamber, allowing for measurement and classification of embryo sex/gender without use of invasive means. The only other methods to determine male from female embryos are though cellular biopsy and pre implantation genetic testing.

Figure 9:
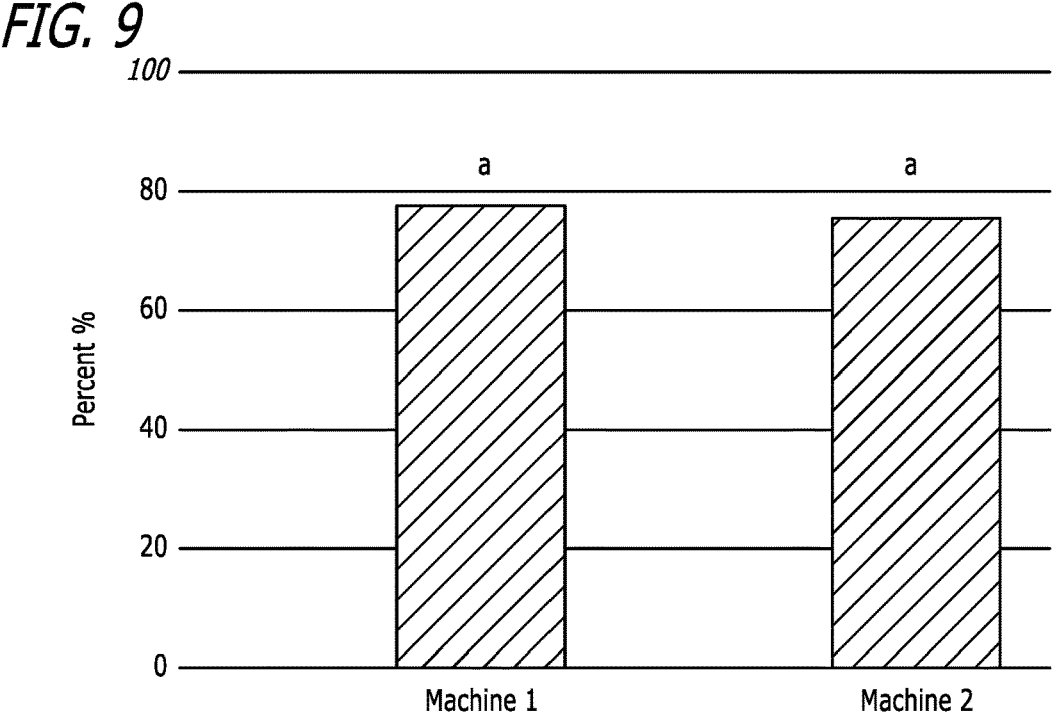
FIG. 9 depicts a bar chart showing sexing success rates using the system of the present invention.

FIG. 9 presents data relating to the success rate of the present invention on embryo sex prediction, wherein two systems were able to provide greater than 70% success by assessment of the embryo's descent time. Further accuracy of the detection of embryo sex is obtained by having the system of the present invention incorporate data relating to the embryo cell number or embryo diameter, which may be obtained by the sensor during the assessment step.

REFERENCES

American Association of Bioanalysts—Embryo Grading Proficiency Testing. http://www.aab-pts.org/pdf/stats/Emb-Ands12013/AEF%20Embryo%20Grading%20Qualitative%201Q2013.pdf Abe H., Yamashita S., Satoh T., Hoshi H. Accumulation of cytoplasmic lipid droplets in bovine embryos and cryo-tolerance of embryos developed in different culture systems using serum-free or serum-containing media. Mol. Reprod. Dev. 2002; 61: 57-66.

Al Inany H, Aboulghar M, Mansour R, Serour G. Meta-analysis of recombinant versus urinary-derived FSH: an update. Hum Reprod. 2003; 18:305-313. doi: 10.1093/humrep/deg088.

Alfarawati S, Fragouli E, Colls P, Wells D. First births after preimplantation genetic diagnosis of structural chromosome abnormalities using comparative genomic hybridization and microarray analysis. Hum Reprod. 2011; 26:1560-74. doi: 10.1093/humrep/der068.

Alfarawati S, Fragouli E, Colls P, Stevens J, Gutiérrez-Mateo C, Schoolcraft W B, Katz-Jaffe M G, Wells D. The relationship between blastocyst morphology, chromosomal abnormality, and embryo gender. Fertil Steril. 2011; 95:520-4.

Baltz J M. Connections between preimplantation embryo physiology and culture. J Assist Reprod Genet. 2013 August; 30(8):1001-7.

Barcelo-Fimbres M., Seidel G. E. Jr. Effects of either glucose or fructose and metabolic regulators on bovine embryo development and lipid accumulation in vitro. Mol. Reprod. Dev. 2007; 74: 1406-1418.

Brezina P R. Preimplantation Genetic Testing in the 21st Century: Uncharted Territory. Clin Med Insights Reprod Health. 2013; 7:17-21.

Brison D R, Houghton F D, Falconer D, Roberts S A, Hawkhead J, Humpherson P G, Lieberman B A, Leese H J. Identification of viable embryos in IVF by non-invasive measurement of amino acid turnover. Hum Reprod 2004; 19:2319-2324.

Bühler K F, Fischer R. Recombinant human LH supplementation versus supplementation with urinary hCG-based LH activity during controlled ovarian stimulation in the long GnRH-agonist protocol: a matched case-control study. Gynecol Endocrinol. 2012 May; 28(5):345-50. doi: 10.3109/09513590.2011.633128.

Centers for Disease Control—Assisted Reproductive Technologies (ART). 2013. http://www.cdc.gov/art/

Chandra A, Martinez G M, Mosher W D, Abma J C, Jones J. Fertility, family planning, and reproductive health of U.S. women: Data from the 2002 National Survey of Family Growth. National Center for Health Statistics. Vital Health Stat 23(25). 2005.

Chavez S L, Loewke K E, Han J, Moussavi F, Colls P, Munne S, Behr B, Reijo Pera R A. Dynamic blastomere behaviour reflects human embryo ploidy by the four-cell stage. Nat Commun. 2012; 3:1251. doi: 10.1038/ncomms2249.

Conaghan J, Chen A A, Willman S P, Ivani K, Chenette P E, Boostanfar R, V L, Adamson G D, Abusief M E, Gvakharia M, Loewke K E, Shen S. Improving embryo selection using a computer-automated time-lapse image analysis test plus day 3 morphology: results from a prospective multicenter trial. Fertil Steril. 2013; 100:412-9.e5. doi: 10.1016/j.fertnstert.2013.04.021.

Das M, Holzer H E. Recurrent implantation failure: gamete and embryo factors. Fertil Steril. 2012 May; 97(5):1021-7. doi: 10.1016/j.fertnstert.2012.02.029.

Deonandan R, Campbell M K, Østbye T, Tummon I. Toward a more meaningful in vitro fertilization success rate. J Assist Reprod Genet. 2000 October; 17(9):498-503.

Ercan C M, Kerimoglu O S, Sakinci M, Korkmaz C, Duru N K, Ergun A. Pregnancy outcomes in a university hospital after legal requirement for single-embryo transfer. Eur J Obstet Gynecol Reprod Biol. 2014; pii: S0301-2115(14)00031-1. doi: 10.1016/j.ejogrb.2014.01.008

Filicori M, Cognigni G. E., Pocognoli P, Tabarelli C, Ferlini F, Perri T, Parmegiani L. Comparison of controlled ovarian stimulation with human menopausal gonadotropin or recombinant follicle-stimulating hormone. Fertil Steril. 2003; 80:390-397. doi: 10.1016/S0015-0282(03)00594-6

Gardner D K, Leese H J. Assessment of embryo viability prior to transfer by the noninvasive measurement of glucose uptake. J Exp Zool 1987; 242:103-105.

Gardner D K, Wale P L. Analysis of metabolism to select viable human embryos for transfer. Fertil Steril. 2013 Mar. 15; 99(4):1062-72. doi: 10.1016/j.fertnstert.2012.12.004.

Geber S, Bossi R, Guimarães F, Valle M, Sampaio M. Effects of transfer of embryos independently cultured in essential and sequential culture media on pregnancy rates in assisted reproduction cycles. J Assist Reprod Genet. 2012 October; 29(10):1097-101. doi: 10.1007/s10815-012-9835-6.Gerris J, De Neubourg D, Mangelschots K, et al. Prevention of twin pregnancy after in-vitro fertilization or intracytoplasmic sperm injection based on strict embryo criteria: a prospective randomized clinical trial. Hum Reprod 1999; 14:2581-2587.

Grace J, El-Toukhy T, Scriven P, Ogilvie C, Pickering S, Lashwood A, Flinter F, Khalaf Y, Braude P. Three hundred and thirty cycles of preimplantation genetic diagnosis for serious genetic disease: clinical considerations affecting outcome. BJOG. 2006; 113:1393-401.

Houghton F D, Hawkhead J A, Humpherson P G, Hogg J E, Balen A H, Rutherford A J, Leese H J. Non-invasive amino acid turnover predicts human embryo developmental capacity. Hum Reprod 2002; 17:999-1005.

Hur Y S, Park J H, Ryu E K, Park S J, Lee J H, Lee S H, Yoon J, Yoon S H, Hur C Y, Lee W D, Lim J H. Effect of micro-vibration culture system on embryo development. J Assist Reprod Genet. 2013; 30:835-41. doi: 10.1007/s10815-013-0007-0.

Kresowik J D, Sparks A E, Van Voorhis B J. Clinical factors associated with live birth after single embryo transfer. Fertil Steril. 2012; 98:1152-6. doi: 10.1016/j.fertnstert.2012.07.1141.

Janvier A, Spelke B, and Barrington K. The Epidemic of Multiple Gestations and Neonatal Intensive Care Unit Use: The Cost of Irresponsibility. J Pediatr 2011; 159: 409-13.

Jones G M, Trounson A, Vella P J, Thouas G A, Lolatgis N, Wood C. Glucose metabolism of human morula and blastocyst-stage embryos and its relationship to viability after transfer. RBM Online 2001; 3:124-132.

Lane M, Gardner D K. Selection of viable mouse blastocysts prior to transfer using a metabolic criterion. Hum Reprod 1996; 11:1975-1978.

Luke B, Brown M B, Wantman E, Lederman A, Gibbons W, Schattman G L, Lobo R A, Leach R E, Stern J E. Cumulative birth rates with linked assisted reproductive technology cycles. N Engl J Med. 2012; 366:2483-91. doi: 10.1056/NEJMoa1110238.

Machtinger R, Racowsky C. Morphological systems of human embryo assessment and clinical evidence. Reprod Biomed Online. 2013; 3:210-21. doi: 10.1016/j.rbmo.2012.10.021.

McArthur S J, Leigh D, Marshall J T, de Boer K A, Jansen R P. Pregnancies and live births after trophectoderm biopsy and preimplantation genetic testing of human blastocysts. Fertil Steril. 2005; 84:1628-36.

Muñoz G, Bongiorni-Malavé I. Influence of dietary protein restriction on ovulation, fertilization rates and pre-implantation embryonic development in mice. J Exp Zool. 1979; 210:253-257.

Racowsky C, Vernon M, Mayer J, Ball G D, Behr B, Pomeroy K O, Ball G D, Behr B, Pomeroy K O, Wininger D, Gibbons W, Conaghan J, Stern J E. Standardization of grading embryo morphology. J Assist Reprod Genet. 2010; 27:437-9. doi: 10.1007/s10815-010-9443-2.

Reynolds K A, Omurtag K R, Jimenez P T, Rhee J S, Tuuli M G, Jungheim E S. Cycle cancellation and pregnancy after luteal estradiol priming in women defined as poor responders: a systematic review and meta-analysis. Hum Reprod. 2013; 28:2981-9. doi: 10.1093/humrep/det306.

Sakkas, D. and Gardner, D. K. Noninvasive methods to assess embryo quality. Curr Opin Obstet Gynecol 2005; 17:283-288.

Scott R T Jr, Upham K M, Forman E J, Hong K H, Scott K L, Taylor D, Tao X, Treff N R. Blastocyst biopsy with comprehensive chromosome screening and fresh embryo transfer significantly increases in vitro fertilization implantation and delivery rates: a randomized controlled trial. Fertil Steril. 2013; 100:697-703. doi: 10.1016/j.fertnstert.2013.04.035.

Staessen C, Platteau P, Van Assche E, Miciels A, Tournaye H, Camus M, Devroey P, Liebaers I, van Steirteghem A: Comparison of blastocyst transfer with and without preimplantation genetic diagnosis for aneuploidy screening in couples with advanced maternal age: a prospective randomized controlled trial. Hum Reprod 2004, 19:2849-2858.

Steptoe P C, Edwards R G, Purdy J M. Clinical aspects of pregnancies established with cleaving embryos grown in vitro. Br J Obstet Gynaecol. 1980; 87:757-68.

Smith A L. Blastocyst culture in human IVF: the final destination or a stop along the way? Theriogenology. 2002; 57:97-107.

Smith G D, Monteiro da Rocha A. Advances in embryo culture systems. Semin Reprod Med. 2012; 30:214-21. doi: 10.1055/s-0032-1311523.

Thompson S M, Onwubalili N, Brown K, Jindal S K, McGovern P G. Blastocyst expansion score and trophectoderm morphology strongly predict successful clinical pregnancy and live birth following elective single embryo blastocyst transfer (eSET): a national study. J Assist Reprod Genet. 2013; 12:1577-81. doi: 10.1007/s10815-013-0100-4.

Van den Abbeel E, Balaban B, Ziebe S, Lundin K, Cuesta M J, Klein B M, Helmgaard L, Arce J C. Association between blastocyst morphology and outcome of single-blastocyst transfer. Reprod Biomed Online. 2013; 4:353-61. doi: 10.1016/j.rbmo.2013.07.006.

Weathers, J. (2008) *Early Indications of Breed Differences for Cryopreservation of Embryos in Cattle*. Master's Thesis. repositories.tdl.org/ttu-ir/bitstream/handle/2346/18883/Weathers_Julie_Thesis.pdf?sequence=1

Weathers, N. Zimmerer N., Penrose L., Graves-Evenson K., Prien, S. The relationship between maternal body fat and pre-implantation embryonic weight: Implications for survival and long-term development in an assisted reproductive environment. Open J Ob Gyn, 2013, 3; 1-5. doi: 10.4236/ojog.2013.35A2001.

What is claimed is:

1. A method of non-invasive determination of the sex of a mammalian embryo, comprising:
   descending at least one embryo through a drop chamber comprising a lumen extending vertically from a media recovery pool; and
   assessing the at least one embryo by measuring the descending at least one embryo through said drop chamber, wherein said assessing step comprises measuring the estimated weight of the at least one embryo descending through a biocompatible media composition for determination of sex of the at least one embryo and further comprise:
   capturing, by way of a sensor, data relating to the descent time of the at least one embryo obtained from measuring the descending at least one embryo;
   processing the data relating to the descent time of the at least one embryo to create a processed embryo data set;
   performing specific gravity detection on the processed embryo data set to detect the weight of the at least one embryo;
   analyzing the at least one embryo to provide a comparative data set of the at least one embryo based on the at least one embryo data sets; and
   classifying the at least one embryo as male or female, based on analyzing the at least one embryo, based on analyzing the at least one embryo, based on their specific gravity; and
   recovering the embryos from a recovery pool having fluid communication with the lumen of the drop chamber, wherein the recovery pool is capable of receiving embryos from the lumen of the drop chamber.

2. The method of claim 1, wherein said assessing step further comprises making a quantitative assessment of the at least one embryo's weight, buoyancy, or density using specific gravity.

3. The method of claim 1, wherein said assessing step comprises measuring the descending at least one embryo by any of a group consisting of: visual means, tagging, markers, computerized means, or combinations thereof.

4. The method of claim 1, wherein the sensor comprises one or more of a group consisting of: a camera, a laser, a photodetection sensor, a fiber optic sensor, a pyrometer, an infrared sensor, an electro-optical sensor, a through-beam sensor, a radiofrequency sensor, an ultrasound sensor, magnification device and combinations thereof.

5. The method of claim 1, further comprising determining the sex of at least one embryo in the blastocyst stage without having detrimental effects on the embryo.

6. The method of claim 1, further comprising utilizing one or more drop chambers, for determining the sex of more than one embryos, each of the one or more drop chambers capable of depositing the more than one embryos into one or more separate recovery pools to allow recovery of the more than one embryos following determination of the sex of the more than one embryos.

7. A computer-readable storage media storing instructions that are executable by a processor to cause a computer to execute operations comprising:
   capturing, by way of a sensor, data relating to the descent time of the at least one embryo obtained from measuring the descending at least one embryo;
   processing the data relating to the descent time of the at least one embryo to create a processed embryo data set;
   performing specific gravity detection on the processed embryo data set to detect the weight of the at least one embryo;
   analyzing the at least one embryo to provide a comparative data set of the at least one embryo based on the at least one embryo data sets; and
   classifying the at least one embryo as male or female, based on analyzing the at least one embryo, based on their specific gravity.

8. The computer-readable storage media of claim 7, wherein the capturing step further comprises, capturing data relating to the descent time of the at least one embryo, said data generated from the sensor capable of observing each of the at least one embryo descending in the lumen of the drop chamber.

9. The computer-readable storage media of claim 8, wherein the sensor comprises one or more of a group consisting of: a camera, a laser, a photodetection sensor, a fiber optic sensor, a pyrometer, an infrared sensor, an electro-optical sensor, a through-beam sensor, a radiofrequency sensor, an ultrasound sensor, and combinations thereof.

10. The computer-readable storage media of claim 7, wherein processing the data relating to the descent time further comprises determining the applicable descent time of the at least one embryo.

11. The computer-readable storage media of claim 7, wherein performing specific gravity detection further comprises calculating the specific gravity of each of the at least one embryo.

12. A system for determining the sex of a mammalian embryo comprising:
   a. insertion of at least one embryo into a drop chamber comprising a lumen extending vertically, said drop chamber further comprising a growth supportive culture media composition, wherein the drop chamber further comprises one or more sensors designed to capture the descent time of the at least one embryo through the drop chamber; and
   b. descent of said at least one embryo through said drop chamber; wherein said descent through said drop chamber allows for measurement of specific gravity of the embryo by descent time of the embryo through a biocompatible media, wherein the at least one embryo passes through a predetermined timing zone of said drop chamber having an upper and lower boundary of said predetermined timing zone, wherein measurement comprises determining the estimated weight of the embryo descending through the growth supportive culture media composition between the upper and lower boundaries of said predetermined timing zone, and c. wherein, the specific gravity measurement is configured to allow for determination of the applicable sex of the embryo.

13. The system of claim 12, wherein the one or more sensors comprises one or more of a group consisting of: a camera, a laser, a photodetection sensor, a fiber optic sensor, a pyrometer, an infrared sensor, an electro-optical sensor, a through-beam sensor, a radiofrequency sensor, an ultrasound sensor, magnification device and combinations thereof.

14. The system of claim 12, further comprising a computer-readable storage media storing instructions that are executable by a processor to cause a computer to execute operations comprising:

capturing, by way of the sensor, data relating to the descent time of the at least one embryo obtained from measuring the descending at least one embryo;

processing the data relating to the descent time of the at least one embryo to create a processed embryo data set;

performing specific gravity detection on the processed embryo data set to detect the weight of the at least one embryo;

analyzing the at least one embryo to provide a comparative data set of the at least one embryo based on the at least one embryo data sets; and classifying the at least one embryo as male or female, based on analyzing the at least one embryo.

15. The system of claim 12, further comprising recovery of the at least one embryo from a recovery pool following assessment of the sex of at least one embryo.

16. The system of claim 14, wherein the sensor comprises one or more of a group consisting of: a camera, a laser, a photodetection sensor, a fiber optic sensor, a pyrometer, an infrared sensor, an electro-optical sensor, a through-beam sensor, a radiofrequency sensor, an ultrasound sensor, magnification device and combinations thereof.

17. The system of claim 12, further comprising utilizing one or more drop chambers, for assessing more than one embryo, each of the one or more drop chambers emptying into a unique recovery pool or specified area to allow determining the sex of the more than one embryo having unique identifications.

* * * * *